United States Patent
Buchholtz et al.

(10) Patent No.: US 7,438,695 B2
(45) Date of Patent: Oct. 21, 2008

(54) SHOCKWAVE SYSTEM AND METHOD FOR OPERATION OF SUCH A SHOCKWAVE SYSTEM

(75) Inventors: Gerhard Buchholtz, Erlangen (DE); Jens Fehre, Hausen (DE); Bernd Granz, Oberasbach (DE); Martin Hoheisel, Erlangen (DE); Werner Kruft, Erlangen (DE); Markus Lanski, Fürth (DE); Matthias Mahler, Erlangen (DE); Christian Meinert, Marloffstein (DE); Thomas Mertelmeier, Erlangen (DE); Ralf Nanke, Neunkirchen (DE); Manfred Rattner, Grossenseebach (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

(21) Appl. No.: 11/478,992

(22) Filed: Jun. 30, 2006

(65) Prior Publication Data
US 2007/0038159 A1 Feb. 15, 2007

(30) Foreign Application Priority Data
Jul. 4, 2005 (DE) ................... 10 2005 031 126

(51) Int. Cl.
*A61H 1/00* (2006.01)

(52) U.S. Cl. .................................................. 601/4
(58) Field of Classification Search ............. 600/26–27; 601/4; 128/630, 732; 434/236, 262
See application file for complete search history.

(56) References Cited

U.S. PATENT DOCUMENTS

| 5,253,168 | A | * | 10/1993 | Berg | 600/301 |
| 5,304,112 | A | * | 4/1994 | Mrklas et al. | 600/27 |
| 5,313,954 | A | * | 5/1994 | Schwarze et al. | 600/515 |
| 2007/0016115 | A1 | * | 1/2007 | Buchholtz et al. | 601/4 |

FOREIGN PATENT DOCUMENTS

DE 202 15 200 U1 2/2003
EP 0 462 295 12/1991

* cited by examiner

*Primary Examiner*—Eric F Winakur
*Assistant Examiner*—Michael T. Rozanski
(74) *Attorney, Agent, or Firm*—Schiff Hardin LLP

(57) ABSTRACT

A shockwave system for treatment of a patient has a detection unit for detection of an indicator correlated with the calmness of the patient, and a device that is operable dependent on the indicator that increases the calmness of the patient. In a method for operation of a shockwave system for treatment of a patient, an indicator correlated with the calmness of the patient is detected and a measure to increase the calmness of the patient is taken dependent on the indicator.

17 Claims, 1 Drawing Sheet

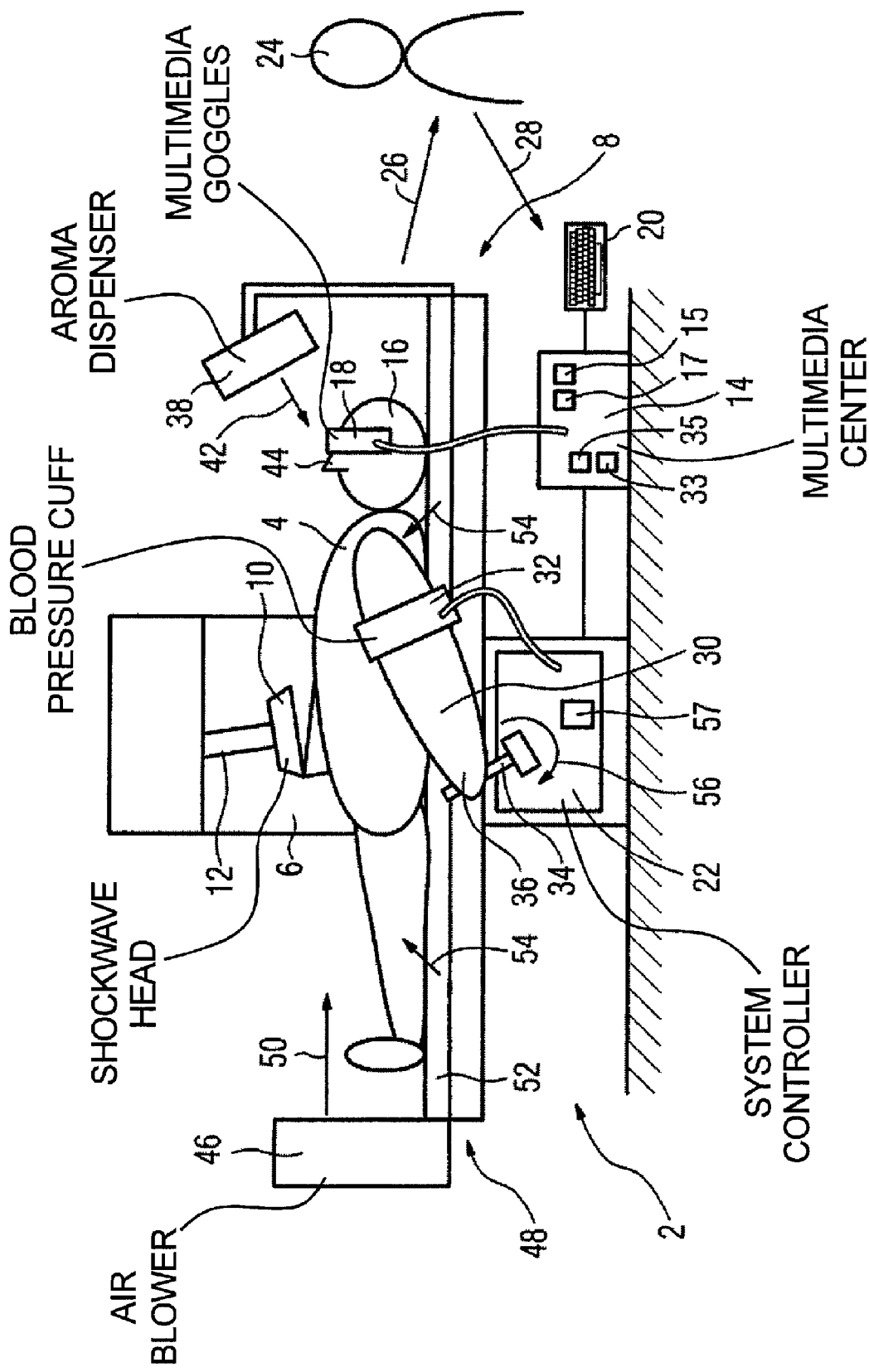

SHOCKWAVE SYSTEM AND METHOD FOR OPERATION OF SUCH A SHOCKWAVE SYSTEM

BACKGROUND OF THE INVENTION

1. Field of the Invention

The present invention concerns a shockwave system and a method for operation of such a shockwave system.

2. Description of the Prior Art

In most medical measures that are conducted on a patient, the patient is exposed to a physical or mental strain. Patients are normally living people and animals. The mental and physical strain of the patient is dependent on many factors and can individually be very different. For example, patients exhibit different physical and mental requirements or cultural differences or have different prior knowledge or experiences with regard to medical measures.

Mental and physical strains of the patient, moreover, have interactions with one another. The physiological stress generated in a patient due to increasing mental discomfort frequently can result in a medical measure lasting longer than planned or even be interrupted, and/or the patient suffering increased side effects after the treatment, etc.

In particular when a therapeutic treatment involving the application of shockwaves to a patient for pain alleviation or calculus disintegration is implemented using a lithotripsy system, the effects of the patient stress on the treatment are particularly pronounced. This has various causes: the smallest movements of the patient require a repositioning of the components of the lithotripsy system, thus a re-alignment of the focal point of the ultrasound shockwave on the treatment target. If the patient feels pains during the treatment, he or she possibly will interrupt the treatment on his or her own or make the aforementioned repositioning necessary due to increased agitation. A repositioning, which is normally implemented with x-rays, in turn leads to increased radiation exposure of the patient. Often under such circumstances, the patient is given an increased medicinal administration of analgesics or narcotics in order to better immobilize the patient.

It is particularly disadvantageous when, for example, a movement caused by agitation of the patient is not noticed by the individual conducting the shockwave therapy. The coupling of the shockwave head to the patient is degraded and the focal point wanders unnoticed from the target. This results in a higher applied energy of the shockwaves or a longer treatment duration, and can even lead to injury of the patient by radiation of ultrasonic shockwaves at unwanted locations, namely by missing the target.

As noted above, in order to minimize the unwanted effects described above of mental and physical stress on the part of the patient, is known to immobilize the patient by adequate medication in the form of anesthetics or analgesics, but this has known risks and side effects. Furthermore, it is known to assist in the pacification of the patient by a detailed communication between the individual conducting the treatment (for example the doctor) and the patient. This places an additional burden on the doctor and; moreover, the success of this approach strongly depends on the sympathy between doctor and patient.

SUMMARY OF THE INVENTION

An object of the present invention is to provide an improved shockwave system and an improved method for operation of such an improved shockwave system.

The invention proceeds from the recognition that a calming atmosphere is generated (for example by music, perfume, etc.) in certain cultures such as cultures termed "far eastern cultures in North America and Europe. People in such atmospheres experience an increased well-being and experience relaxation in a mental and physical regard.

With regard to the shockwave system, the above object is therefore achieved by a shockwave system for treatment of a patient with a detection unit to detect an indicator correlated with the well-being of the patient and with a device to increase the calmness (serenity, composure, tranquility, lack of excitement, etc.) of the patient, that is operable dependent on the indicator.

With the detection unit it is possible to initially detect actual or objective information about the calmness of the patient by means of the indicator. The device to increase the calmness of the patient can thus be controlled (namely operated dependent on the indicator) in order to increase the calmness of the patient. A feedback from the device to the patient or his or her calmness is thus provided by the indicator. In the inventive shockwave system, the calmness of the patient thus can be indirectly determined via the indicator and the patient's calmness can be increased as needed.

The doctor is relieved of the burden of monitoring the calmness of the patient as well as from initiating or participating in measures that increase the calmness of the patient.

As a result of increasing the calmness well-being of the patient, his or her therapy acceptance increases and better therapy results are achieved in form of shorter therapy times, less post-treatment or fewer side effects.

Since the calmness of a patient is influenced by a number of factors, a wide range of detection units of various types is conceivable. The following enumeration can thus should be understood as only exemplary. The detection of a single indicator value or a number of indicator values simultaneously is naturally possible.

The detection unit can be a selection unit to select a value of the indicator. The indicator correlated with the calmness of the patient in this context can be, for example, the designation of his or her favorite color, his or her favorite music, his favorite scent or the like. The individual operating the selection unit, for example the doctor operating the shockwave system or the patient himself or herself, thus himself knows what increases the calmness of the patient and provides a corresponding indicator value.

In this context, a selection unit can be a menu-controlled device for music, color, image, scent selection or the like. The detection unit could also, for example, be a joystick, slide controller, mouse or the like operable by the patient with which the patient provides the aforementioned indicators or provides as an indicator the volume of music, brightness of an image, room illumination or the like. The selection unit or the detection unit alternatively can be an electronic case history (anamnesis) sheet of the doctor or an interface with the patient record containing record indicators correlated with the calmness (or lack thereof) of the patient. Such a detection unit could, for example, detect the anatomical conditions of the patient from the patient record as an indicator. The device could then be an adjustable patient bed that is adapted to the patient in terms of its settings.

In the examples just cited, the indicators are essentially consciously selected by the patient or doctor. A conscious or targeted increase of the calmness thus occurs. This corresponds to a voluntary feedback or, in other words, a feedback from the patient or doctor to the device.

As devices for increasing the calmness, audio devices, lights, temperature regulators for the room temperature, volume controllers, scent generators or the like that are operated dependent on the indicator are suitable for use with such selection units.

The detection unit alternatively can be a measurement value detector detecting a measurement value at the patient as an indicator. The invention makes use of the fact that physiological attributes of the patient change dependent on his calmness. For example, skin resistance, skin temperature, muscle tone, heart rate, brain waves, blood pressure, or the like exhibit such a change. Measurement value detectors can be pulse, blood pressure, temperature, skin moisture measurement devices or the like. Pressure sensors that measure the degree of force with which the patient clasps a grip are also conceivable.

In contrast to the above examples, essentially unconscious influencing variables on the patient are hereby detected. The device to increase the calmness is then operated automatically, without interventions of the patient or doctor. This corresponds to an involuntary feedback from the patient to the device.

As already mentioned above for the detection unit, manifold possibilities are likewise conceivable for the device to increase the calmness, which is why the following enumeration again should be understood as only exemplary. The cited alternatives can be used individually or in combination.

The device to increase the calmness can be a multimedia center. The invention utilizes the fact that a patient is particularly strongly influenced in mental terms by multimedia effects. Multimedia effects act on a number of stimulus centers of the patient, for example optical and acoustical. Due to the connection between psyche and physiology, a multimedia center is therefore particularly suitable to increase the calmness of the patient. Stimuli to which the patient is exposed can be adapted to one another particularly well in a multimedia center, or can be presented in combination to the patient. Techniques such as, for example, hypnosis or autogenous training can be applied via a multimedia center to increase the calmness of the patient.

The device to increase the calmness can be a device for application of aromas or flavors (scent or taste substances) to the patient. For example, in addition to a multimedia center, warm air or fresh air as well as scents, for example, can be supplied to the patient in order, for example, to simulate mountain air, a sea coast or the like. For example, if the patient likes to stay in the mountains, this can be suggested to him or her via multimedia in connection with a cool air draft and corresponding scent. The patient experiences a situation in which he or she feels positive and thus the calmness increases.

The device to increase the calmness of the patient can be a device for physiotherapeutic treatment of the patient. For example, the patient can be massaged, treated with heat or cold, irradiated with radiant heat, light, magnetic or electrical fields, etc.

The shockwave system can have a system controller to influence the shockwave parameters dependent on the indicator. A feedback between the patient or his or her calmness or the indicator is thus possible by influencing the shockwave parameters. Depending on the detection of the indicator as mentioned above, the patient can voluntarily or involuntarily influence his or her calmness in the context of the shockwave therapy so as to produce an increased calmness.

With regard to the method, the above object is achieved by a method for operation of a shockwave system for treatment of a patient, in which an indicator correlated with the calmness of the patient is detected and a measure to increase the calmness of the patient is initiated dependent on the indicator.

The advantages of the inventive method have already been explained in detail in connection with the shockwave system.

Naturally neither the system nor the method are limited to a single indicator (and therewith to a single detection unit) and to a single device for increasing the well-being of the patient.

With regard to the method it should again be mentioned that the patient and/or the operator of the shockwave system can provide the indicator manually. The patient and/or operator thus retains control over the measures taken with regard to the calmness of the patient in the context of the shockwave therapy. An example of this is the aforementioned music selection by the patient.

Alternatively or additionally, the indicator can be detected automatically. This is primarily advantageous for indicators for which the manual detection is difficult or impossible, such as the detection of a measurement value at the patient, such as a cyclical blood pressure measurement. The automatic detection of the indicator offers the advantage that patient and/or operator of the shockwave system are unburdened of this task. A selection of the measure thus likewise ensues automatically.

As described above, as a calmness increasing measure a multimedia signal can be transmitted to the patient, an aroma and/or flavor can be administered to the patient and/or a physiotherapeutic measure on the patient can be taken.

If the shockwave parameters are varied as a measure, a shorter therapy time is achieved by, for example, higher ultrasound power.

DESCRIPTION OF THE DRAWINGS

The single FIGURE shows a patient in a shockwave system in accordance with the invention during the implementation of lithotripsy.

DESCRIPTION OF THE PREFERRED EMBODIMENTS

The FIGURE shows a lithotripsy system 2 with a patient 4 on whom a shockwave lithotripsy is to be conducted. The lithotripsy system 2 has a base unit 6 with an integrated system controller 22 on which a bed 8 and a shockwave head 10 are carrier arms on a carrier arm 12 being visible in the FIGURE.

The lithotripsy system 2 also has a multimedia center 14 with multimedia goggles 18 connected thereto and placed on the head 16 of the patient.

Furthermore, the multimedia center 14 has an input unit connected with in the form of a keyboard 20. The multimedia center 14 is connected with the system controller 22 for data exchange.

Before beginning the lithotripsy on the patient 3, a doctor 24 directing the treatment conducts an anamnesis on the patient 4 (indicated in the FIGURE by the arrow 26). Among other things, the doctor 24 determines various preferences of the patient 4 as indicators that, according to statements of the patient 4, are particularly pleasant to him or her and thus increase his or her calmness and thus are correlated therewith.

In the exemplary embodiment, these are a selection of specific musical pieces 15 which particularly please the patient 4 and the statement that the patient 4 enjoys time at the ocean. The doctor 24 enters a song title and the keyword 17 "ocean environment" (indicated by the arrow 28) into the multimedia center 14 via the keyboard 20 as indicators correlated with the calmness of the patient.

Since the patient 4 likes to stay at the ocean, an image of a coastal landscape is displayed to the patient 4 via the multimedia goggles 18. The patient 4 relaxes by viewing the image and hearing his or her favorite music played via the multimedia goggles 18.

Furthermore, a blood pressure cuff 32 fastened on the arm 30 of the patient is connected to the system controller 22. Moreover, a handle 34 which the patient 4 grasps with his or her hand 36 is mounted on the system controller 22.

To further relax the patient 4 or to increase the calmness of the patient 4, an aroma dispenser 38 is attached to the bed 8 via a carrier arm 40, from which aroma dispenser 38 scents are expelled in the direction of the arrow 42 toward the nose 44 of the patient. The scents, in the example typical aromas of a coastal region, underscore the visual impression of the patient 4 (that he or she is located in a coastal region). The calmness of the patient 4 is further increased. The previous indicators were voluntarily or manually provided by the patient 4.

During the entire shockwave lithotripsy, blood pressure, pulse and skin moisture of the patient are measured via the blood pressure cuff 32 as measurement quantities 33, which—in contrast to the manual specification above—allow feedback about the calmness of the patient 4 in an automatic manner. Furthermore, pressure sensors (not shown) can be integrated into the grip 34 that detect, as a measurement quantity, the muscle tone 35 of the patient 4 upon grasping the grip 34. The detected measurement quantities likewise enter into the system controller 22 as indicators correlated with the calmness of the patient.

Given decreasing calmness of the patient during the shockwave lithotripsy, established from changed values of blood pressure, pulse, skin moisture etc. as indicators, measures in order to increase the calmness of the patient 4 again are introduced by the system controller 22. For this, initially warm air that is pleasant for the patient 4 is supplied (indicated by the arrow 50) to the patient in stages from a blower 46 at the foot 48 of the bed 8. Moreover, the patient 4 is massaged (indicated by the arrows 54) by a massage (vibrating) pad 52 located on the bed 8.

If the calmness of the patient drops again, for example due to the ultrasonic shockwaves emitted by the shockwave head 10 that are felt too strongly by the patient 4, the patient 4 consciously moves the handle 36 in the direction of the arrow 56 and thus provides an indicator in order to reduce the energy level of the ultrasonic shockwaves as a shockwave parameter 57 to a measure that is comfortable or bearable for the patient 4. Given progressive stone treatment, the discomfort caused by the ultrasonic shockwaves in the patient 4 decreases, so the patient 4 operates the handle 34 opposite the direction of the arrow 56 in order to increase the energy level of the shockwaves again and thus to achieve a faster treatment conclusion, which likewise increases the patient's calmness.

Although modifications and changes may be suggested by those skilled in the art, it is the intention of the inventors to embody within the patent warranted hereon all changes and modifications as reasonably and properly come within the scope of their contribution to the art.

We claim as our invention:

1. A shockwave system for treatment of a patient, comprising:
   a shockwave delivery apparatus configured to receive a patient in physical inter-relation with the shockwave delivery apparatus to administer shockwaves to the patient during a portion of a shockwave procedure;
   a detection unit configured to interact with the patient in said physical inter-relation with the shockwave delivery apparatus to detect an indicator correlated with calmness of the patient during said shockwave procedure; and
   a device other than said shockwave delivery apparatus, that operates dependent on said indicator to automatically, non-manually interact with the patient in said physical inter-relation with the shockwave delivery apparatus to increase the calmness of the patient during said shockwave procedure.

2. A shockwave system as claimed in claim 1 wherein said detection unit comprises a selection unit allowing selection of a value of said indicator.

3. A shockwave system as claimed in claim 1 wherein said detection unit is a measurement value detector configured to interact with the patient to detect a measurement value as said indicator.

4. A shockwave system as claimed in claim 1 wherein said device is a multimedia center that produces humanly perceptible outputs to increase the calmness of the patient.

5. A shockwave system as claimed in claim 1 wherein said device comprises a device for exposing the patient to an aroma.

6. A shockwave system as claimed in claim 1 wherein said device is a device for exposing the patient to a flavor.

7. A shockwave system as claimed in claim 1 wherein said device is a device for applying physiotherapeutic treatment to the patient.

8. A shockwave system as claimed in claim 1 wherein said shockwave delivery apparatus comprises a lithotripter operable according to shockwave parameters, and a system controller that influences said shockwave parameters of said lithotripter dependent on said indicator.

9. A method for operating a shockwave system for treatment of a patient with shockwaves, comprising the steps of:
   placing a patient in physical inter-relation with a shockwave delivery apparatus and, during a portion of a shockwave procedure, administering shockwaves to the patient with the shockwave delivery apparatus;
   detecting an indicator correlated with calmness of the patient in said physical inter-relation with the shockwave delivery apparatus; and
   with a device other than said shockwave delivery apparatus, automatically, non-manually interacting with the patient in said physical inter-relation with the shockwave delivery apparatus, dependent on said indicator, to increase the calmness of the patient during said shockwave procedure.

10. A method as claimed in claim 9 comprising manually providing said indicator by the patient.

11. A method as claimed in claim 9 comprising manually providing the indicator by an operator of the shockwave system.

12. A method as claimed in claim 9 comprising automatically, non-manually detecting said indicator.

13. A method as claimed in claim 9 comprising exposing said patient to a multimedia signal to increase the calmness of the patient during said shockwave procedure.

14. A method as claimed in claim 9 comprising exposing said patient to a aroma to increase the calmness of the patient during said shockwave procedure.

15. A method as claimed in claim 9 comprising exposing said patient to a flavor to increase the calmness of the patient during said shockwave procedure.

16. A method as claimed in claim 9 comprising exposing said patient to a physiotherapeutic measure to increase the calmness of the patient during said shockwave procedure.

17. A method as claimed in claim 9 comprising administering said shockwaves to the patient dependent on shockwave parameters, and altering said shockwave parameters dependent on said indicator to increase the calmness of the patient during said shockwave procedure.

* * * * *